US 6,611,959 B1

(12) United States Patent
Lando

(10) Patent No.: US 6,611,959 B1
(45) Date of Patent: Sep. 2, 2003

(54) HEADWEAR WITH EYE PROTECTOR

(76) Inventor: Ronald Lando, 55 Aptos Ave., San Francisco, CA (US) 94127

( * ) Notice: Subject to any disclaimer, the term of this patent is extended or adjusted under 35 U.S.C. 154(b) by 0 days.

(21) Appl. No.: 10/151,131

(22) Filed: May 18, 2002

(51) Int. Cl.[7] ................................................. A61F 9/00
(52) U.S. Cl. ............................... 2/10; 2/209.13; 2/445; 2/453
(58) Field of Search ........................ 2/422, 453, 454, 2/445, 410, 209.13, 10; 351/59, 155

(56) References Cited

U.S. PATENT DOCUMENTS

| | | | | | |
|---|---|---|---|---|---|
| 871,762 | A | * | 11/1907 | Meyrowitz | 2/445 |
| 2,502,162 | A | * | 3/1950 | Malcom | 2/453 |
| 2,609,538 | A | * | 9/1952 | Jackson | 2/453 |
| 5,278,999 | A | * | 1/1994 | Brown et al. | 2/209 |
| 5,289,592 | A | * | 3/1994 | Paivarinta | 2/431 |
| 5,323,493 | A | * | 6/1994 | Ogiba | 2/422 |
| 6,253,388 | B1 | | 7/2001 | Lando | |
| 6,308,336 | B1 | * | 10/2001 | Stephenson et al. | 2/209.13 |

FOREIGN PATENT DOCUMENTS

EP    408344 A2 *  1/1991  ........... A42B/03/00

* cited by examiner

*Primary Examiner*—Rodney M. Lindsey
(74) *Attorney, Agent, or Firm*—Jack Lo

(57) ABSTRACT

The present headwear with eye protector is comprised of a helmet with slots on either side. The slots may be fixed to the helmet, or provided in housings hinged to the helmet. An eyewear is attached to the slots. The eyewear is comprised of a pair of lenses hinged to respective arms that slide into the slots. A pair of connectors attached to the inner ends of the lenses releasably connect the lenses together. The lenses are removable from the eyes by separating their inner ends, and pivoting them away without detaching them from the helmet. The lenses are adjustable fore and aft by sliding the arms within the slots, and are adjustable up and down by tilting the housings. Additional slots may be provided on the housing in a vertical column for further adjusting the height of the lenses.

9 Claims, 3 Drawing Sheets

HEADWEAR WITH EYE PROTECTOR

BACKGROUND OF THE INVENTION

1. Field of the Invention

The invention broadly relates to eyewear and helmets.

2. Prior Art

The common types of helmets include full-face and open-face helmets. Although both types of helmets may include a transparent face shield, some people prefer to wear goggles. However, goggles are inconvenient to wear because they are typically secured by an elastic strap that wraps around the back of the helmet. The elastic strap makes such goggles difficult to put on.

BRIEF SUMMARY OF THE INVENTION

The present headwear with eye protector is comprised of a helmet with slots on either side, The slots may be fixed to the helmet, or provided in housings hinged to the helmet. An eyewear is attached to the slots. The eyewear is comprised of a pair of lenses hinged to respective arms that slide into the slots. A pair of connectors attached to the inner ends of the lenses releasably connect the lenses together. The lenses are removable from the eyes by separating their inner ends, and pivoting them away without detaching them from the helmet. The lenses are adjustable fore and aft by sliding the arms within the slots, and are adjustable up and down by tilting the housings. Additional slots may be provided on the housing in a vertical column for further adjusting the height of the lenses.

DETAILED DESCRIPTION OF THE INVENTION

Figure 1:
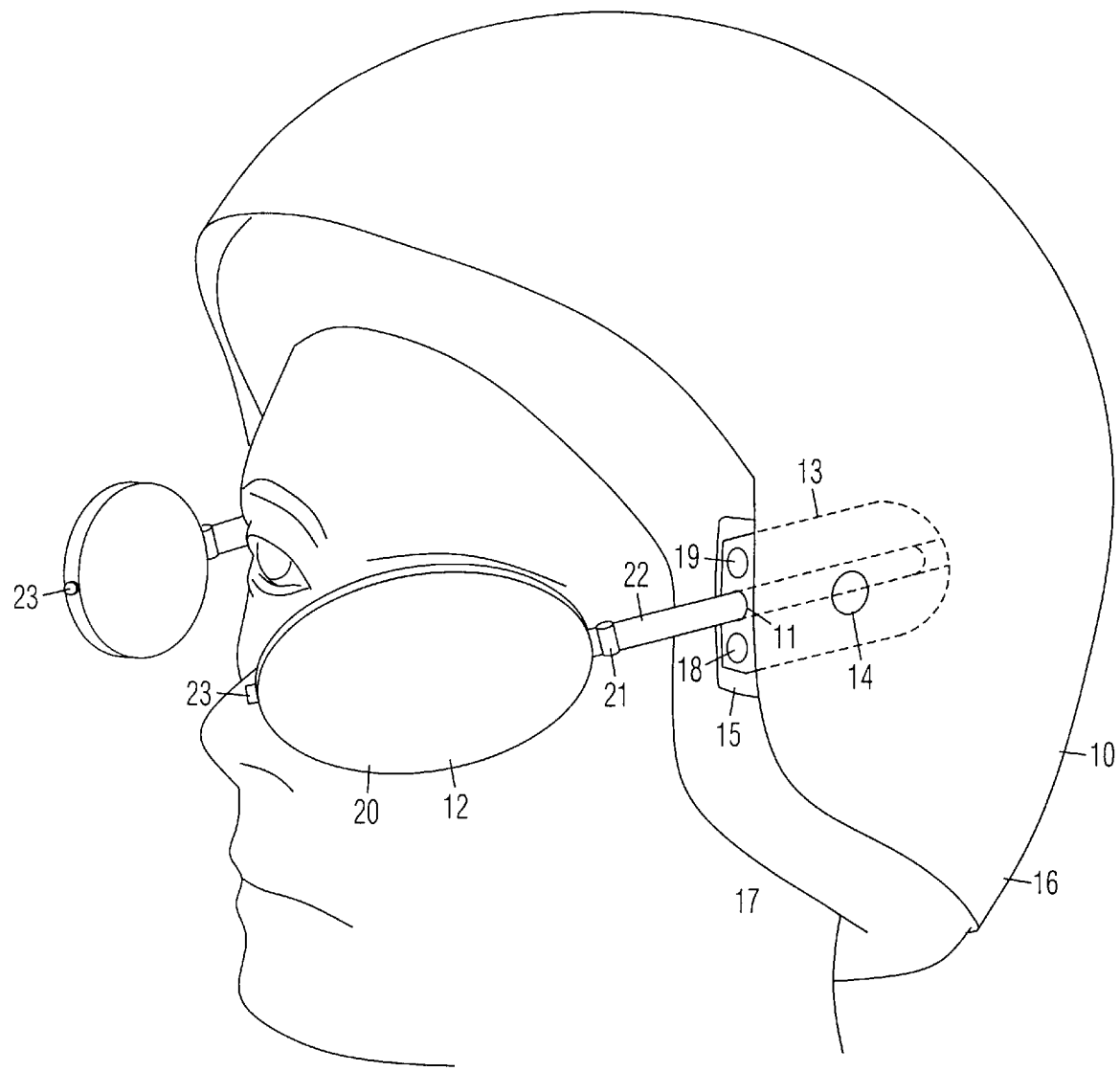
FIG. 1 is a side perspective view of the present headwear when the eyewear is positioned away from the eyes.

FIG. 1:

A preferred embodiment of the present headwear is shown in a side perspective view in FIG. 1. It is comprised of a helmet 10 with slots 11 on either side, and an eyewear 12 attached to slots 11.

Slots 11 are provided in a pair of housings 13 (one shown) hinged to either side of helmet 10 by a pivot 14. In this example, housings 13 are positioned in respective pockets 15 (one shown) between a shell 16 and a lining 17 of helmet 10. Alternatively, housings 13 may be attached outside shell 16. Additional slots 18 and 19 are provided in respective housings 13 in a vertical column.

Eyewear 12 is comprised of a pair of lenses 20 with outer ends hinged by pivots 21 to respective arms 22 that are positioned in slots 11. Lenses 20 may be adjusted fore and aft by sliding arms 22 within slots 11. Lenses 20 may be adjusted up and down to fit different users by pivoting housings 13, or by positioning arms 22 in slots 18 or 19. A pair of connectors 23 attached to the inner ends of lenses 20 releasably connect lenses 20 together. Connectors 23 are preferably comprised of magnets, such as neodymium-iron-boron magnets, for maximum convenience when connecting and disconnecting. When connectors 23 are attached together, they form a bridge between lenses 20.

Lenses 20 are removable from the eyes by separating their inner ends, and pivoting them away without detaching them from helmet 10, as shown in FIG. 1. Lenses 20 are adjustable fore and aft by sliding arms 22 within slots 11, and are adjustable up and down by tilting housings 13. Additional slots 18 and 19 on respective housings 13 are provided for receiving arms 22 to enable further height adjustment. Lenses 20 may be removed from helmet 20 if desired by sliding out arms 22.

Figure 2:
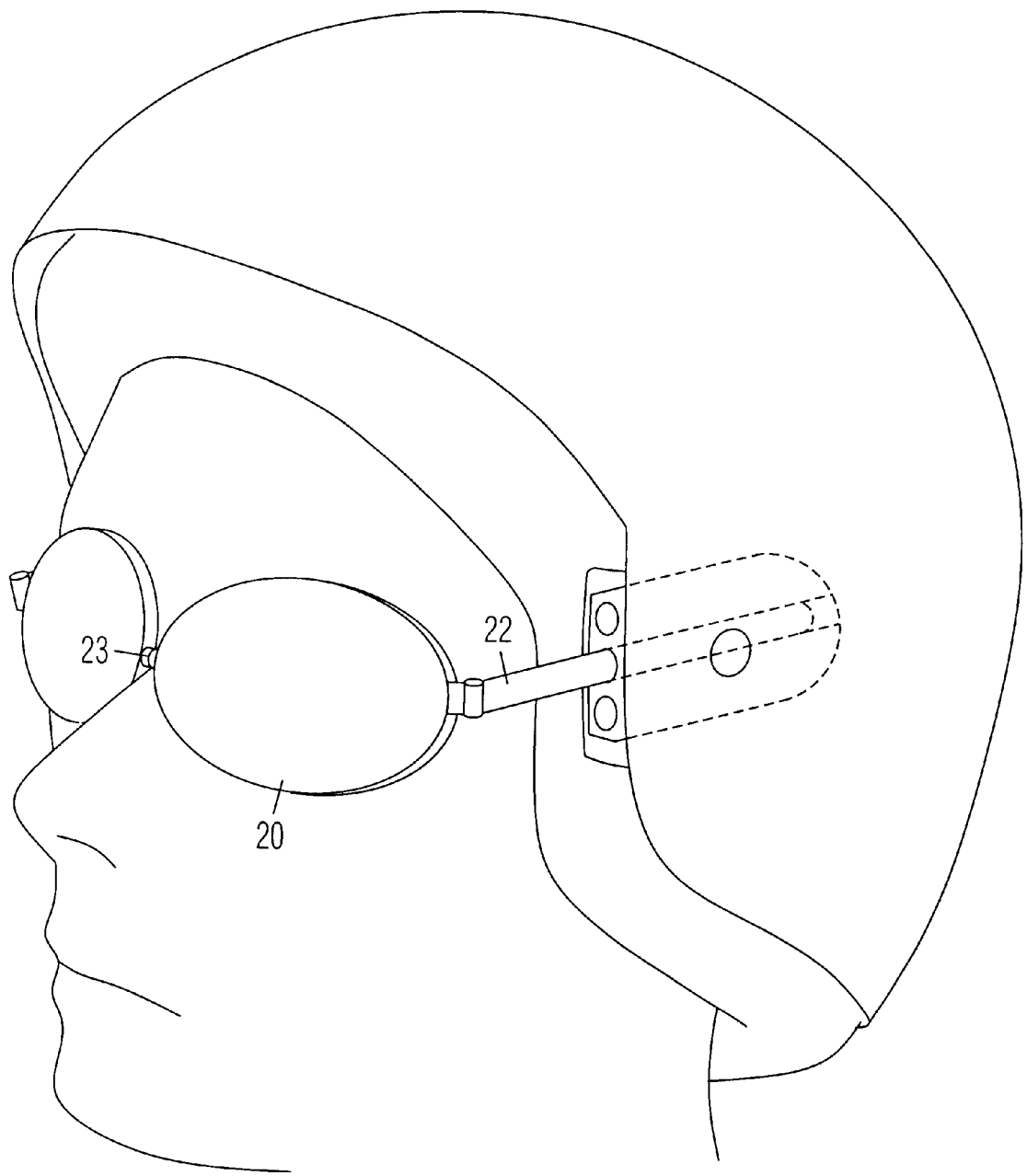
FIG. 2 is a side perspective view thereof when the eyewear is positioned against the eyes.

FIG. 2:

Lenses 20 are shown in FIG. 2 connected together with connectors 23.

Figure 3:
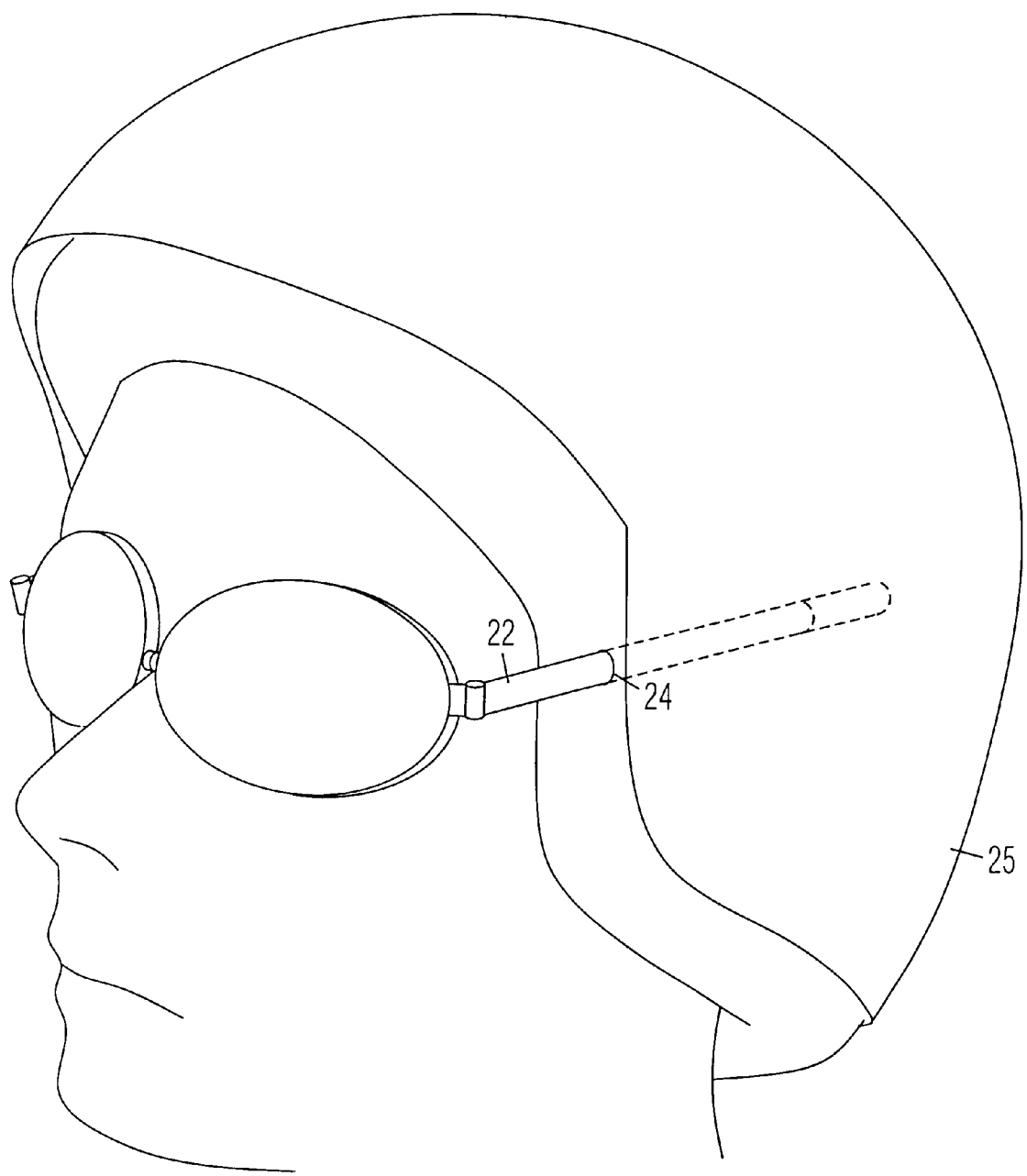
FIG. 3 is a side perspective view of an alternative embodiment thereof.

FIG. 3:

In an alternative embodiment shown in FIG. 3, a pair of fixed slots 24 (one shown) are provided on either side of a helmet 25. Arms 22 are received in respective slots 24. Additional fixed slots (not shown) may be provided along a vertical column.

Although the foregoing description is specific, it should not be considered as a limitation on the scope of the invention, but only as an example of the preferred embodiment. Many variations are possible within the teachings of the invention. Therefore, the scope of the invention should be determined by the appended claims and their legal equivalents, not by the examples given.

I claim:

1. A headwear, comprising:
   a helmet;
   slots on either side of said helmet; and
   an eyewear attached to said slots, wherein said eyewear is comprised of:
   a pair of lenses with outer ends respectively hinged to a pair of arms, wherein said arms are positioned in respective slots in said helmet; and
   a pair of connectors attached to respective inner ends of said lenses to releasably connect said lenses together, wherein said lenses are separable and pivotable outwardly by disconnecting said connectors.

2. The headwear of claim 1, wherein said connectors are comprised of magnets.

3. The headwear of claim 1, wherein said arms are adjustable fore and aft within said slots.

4. The headwear of claim 1, further including additional slots arranged in a vertical column in respective housings, wherein said arms are attachable to any corresponding pair of slots for height adjustment.

5. A headwear, comprising:
   a helmet;
   a pair of housings pivoted on either side of said helmet;
   slots in respective housings; and
   an eyewear attached to said slots, wherein said eyewear is comprised of:
   a pair of lenses with outer ends respectively hinged to a pair of arms, wherein said arms are positioned in respective slots in said helmet; and
   a pair of connectors attached to respective inner ends of said lenses to releasably connect said lenses together, wherein said lenses are separable and pivotable outwardly by disconnecting said connectors.

6. The headwear of claim 5, wherein said connectors are comprised of magnets.

7. The headwear of claim 5, wherein said arms are adjustable fore and aft within said slots.

8. The headwear of claim 5, wherein said arms are pivotable up and down with said housings.

9. The headwear of claim 5, further including additional slots arranged in a vertical column in respective housings, wherein said arms are attachable to any corresponding pair of slots for height adjustment.

* * * * *